(12) United States Patent
Steenhoek et al.

(10) Patent No.: US 8,999,429 B2
(45) Date of Patent: Apr. 7, 2015

(54) SYSTEMS AND METHODS FOR COATING MEASUREMENT

(71) Applicant: Axalta Coating Systems IP Co., LLC, Wilmington, DE (US)

(72) Inventors: Larry Eugene Steenhoek, Wilmington, DE (US); Allan Blase Joseph Rodrigues, Bloomfield Hills, MI (US); Gerard T. Brosmer, Wilmington, DE (US); David Lee Griffus, Grand Blanc, MI (US)

(73) Assignee: Axalta Coating Systems IP Co., LLC, Wilmington, DE (US)

( * ) Notice: Subject to any disclaimer, the term of this patent is extended or adjusted under 35 U.S.C. 154(b) by 0 days.

(21) Appl. No.: 14/154,360

(22) Filed: Jan. 14, 2014

(65) Prior Publication Data
US 2014/0127395 A1   May 8, 2014

Related U.S. Application Data

(62) Division of application No. 13/509,917, filed as application No. PCT/US2010/052869 on Oct. 15, 2010, now Pat. No. 8,771,785.

(60) Provisional application No. 61/287,737, filed on Dec. 18, 2009.

(51) Int. Cl.
*B05D 5/00* (2006.01)
*G01N 33/32* (2006.01)
*G01N 21/25* (2006.01)
*G01N 21/55* (2014.01)
(Continued)

(52) U.S. Cl.
CPC ............... *G01N 33/32* (2013.01); *G01N 21/25* (2013.01); *G01N 21/55* (2013.01); *G01N 21/57* (2013.01); *G01N 21/8422* (2013.01)

(58) Field of Classification Search
None
See application file for complete search history.

(56) References Cited

U.S. PATENT DOCUMENTS

| 4,626,474 A | 12/1986 | Kim et al. |
| 5,151,751 A | 9/1992 | Nakajima et al. |

(Continued)

FOREIGN PATENT DOCUMENTS

| CN | 1500564 A | 6/2004 |
| JP | 2005071525 A | 3/2005 |

(Continued)

OTHER PUBLICATIONS

SIPO, Chinese Office Action issued in Application No. 201080057527.8, dated Dec. 27, 2013.

(Continued)

*Primary Examiner* — Erma Cameron
(74) *Attorney, Agent, or Firm* — Ingrassia Fisher & Lorenz, P.C.

(57) ABSTRACT

Methods and systems for coating measurements are provided. A system for obtaining characteristics of a target coating layer include a clearcoat layer having a first surface and a second surface. A removable front support layer has an upper surface and a lower surface, where the lower surface is affixed over at least a portion of the second surface of the clearcoat layer. A back support layer has an inner surface and an outer surface, and at least a portion of the inner surface includes an adhesive layer. A separation layer is affixed over at least a portion of the adhesive layer, and the separation layer is removable from the adhesive layer.

20 Claims, 6 Drawing Sheets

(51) Int. Cl.
*G01N 21/57* (2006.01)
*G01N 21/84* (2006.01)

(56) References Cited

U.S. PATENT DOCUMENTS

| | | |
|---|---|---|
| 5,371,599 A | 12/1994 | Falcoff |
| 5,633,362 A | 5/1997 | Nagarajan et al. |
| 5,686,276 A | 11/1997 | Laffend et al. |
| 5,821,092 A | 10/1998 | Nagarajan et al. |
| 6,042,678 A | 3/2000 | Johnson et al. |
| 6,083,335 A | 7/2000 | Scullin et al. |
| 6,336,988 B1 | 1/2002 | Enlow et al. |
| 6,579,397 B1 | 6/2003 | Spain et al. |
| 6,720,459 B2 | 4/2004 | Sunkara et al. |
| 6,905,727 B2 | 6/2005 | Spitzer et al. |
| 6,977,291 B2 | 12/2005 | Sunkara et al. |
| 6,995,843 B2 | 2/2006 | Janssen et al. |
| 2001/0023004 A1* | 9/2001 | Shvartsman et al. ........ 428/41.4 |
| 2004/0123941 A1 | 7/2004 | Spain et al. |
| 2004/0123942 A1 | 7/2004 | Spain et al. |
| 2004/0209057 A1 | 10/2004 | Enlow et al. |
| 2004/0258923 A1 | 12/2004 | Sormani et al. |
| 2006/0151347 A1 | 7/2006 | Grossman |
| 2007/0098943 A1 | 5/2007 | Truog et al. |
| 2007/0237891 A1 | 10/2007 | Sugiura et al. |
| 2008/0138627 A1 | 6/2008 | Swarup et al. |
| 2008/0314500 A1 | 12/2008 | Boers et al. |
| 2009/0213120 A1 | 8/2009 | Nisper et al. |

FOREIGN PATENT DOCUMENTS

| | | |
|---|---|---|
| WO | 9222619 A1 | 12/1992 |
| WO | 2004030939 A1 | 4/2004 |

OTHER PUBLICATIONS

ISA USPTO, International Search Report and Written Opinion for International Application No. PCT/US10/52869, mailed Dec. 20, 2010.

Michigan Lake & Stream Associations. "The Secchi Disk—What is it?" Dec. 21, 2007. http://web.archive.org/we2007122121202139/ http://www.miswa.org/secchi.htm Para 1-3; figure.

Leneta Company. "Special Substrates for coating Tests/Spray Monitors/Self-Adhering Hiding Power Labels" http://opacity.leneta.com/item/spray-monitors/form-m33-spray-monitor/m33.

ISA USPTO, International Preliminary Report on Patentability for International Application No. PCT/US10/52869, mailed Jun. 28, 2012.

USPTO, Non-final Office Action for U.S. Appl. No. 13/509,917, mailed Aug. 15, 2013.

Response to non-final Office Action for U.S. Appl. No. 13/509,917, dated Nov. 13, 2013.

USPTO, Notice of Allowance for U.S. Appl. No. 13/509,917, mailed Dec. 13, 2013.

SIPO, Chinese Second Office Action issued in Application No. 201080057527.8, dated Jun. 18, 2014.

* cited by examiner

SYSTEMS AND METHODS FOR COATING MEASUREMENT

CROSS-REFERENCES TO RELATED APPLICATIONS

This is a divisional application of U.S. patent application Ser. No. 13/509,917, filed May 15, 2012, which was the National State of Patent Cooperation Treaty Application No. PCT/US10/52869, filed Oct. 15, 2010, which claims the benefit of U.S. Provisional Application Ser. No. 61/287,737, filed Dec. 18, 2009.

TECHNICAL FIELD

The present invention is directed to a method for obtaining characteristics of a target coating layer. The present invention is also directed to a system for obtaining characteristics of the target coating layer.

BACKGROUND

Surface coatings on a substrate can comprise multiple coating layers, such as one or more primer layers, one or more color coat layers, and one or more clearcoat layers. An initial coating layer is usually a primer layer for providing adhesion to the substrate and protection. The color coat layers are typically applied over the primer layers for further protection and for providing desired color and appearance effects. Typically, the primer layers are formed from one or more coating compositions having corrosion inhibiting compound and pigments. The color coat layers are formed from one or more color coating compositions that utilize one or more pigments or effect pigments to impart the desired color or appearance, such as solid, metallic, pearlescent effect, gloss, or distinctness of image, to the substrate, such as a vehicle body. Metallic flakes, such as aluminum flakes are commonly used to produce coatings having flake appearances, texture, sparkle, glint and glitter as well as the enhancement of depth perception in the coatings imparted by the flakes. In certain instances, a unilayer coating ("unicoat") can be applied over the substrate which contains the corrosion inhibiting compound and any optional coloring pigments. The clearcoat layers can be formed from one or more clearcoat compositions for providing further protection and desired appearance, such as mar and scratch resistance, high gloss and distinctness of image.

The surface coatings are typically formed by sequentially applying selected coating compositions for the desired coating layers and cure or dry the coating layers sequentially or simultaneously.

Currently, characteristics of the color coat, color coat layers are typically measured after the one or more clearcoat layers are applied and formed over the color coat layers that are already formed. In addition, other objects, desirable features and characteristics will become apparent from the subsequent summary and detailed description, and the appended claims, taken in conjunction with the accompanying drawings and this background.

SUMMARY

Methods and systems for coating measurements are provided. In an exemplary embodiment, a system for obtaining characteristics of a target coating layer include a clearcoat layer having a first surface and a second surface. A removable front support layer has an upper surface and a lower surface, where the lower surface is affixed over at least a portion of the second surface of the clearcoat layer. A back support layer has an inner surface and an outer surface, and at least a portion of the inner surface includes an adhesive layer. A separation layer is affixed over at least a portion of the adhesive layer, and the separation layer is removable from the adhesive layer.

In another embodiment, a method for obtaining characteristics of a target coating layer are provided. The method includes providing a measurement system including:

a clearcoat layer with a first surface and a second surface;

a removable front support layer with a lower surface and an upper surface, where the lower surface is affixed over at least a portion of the second surface of the clearcoat layer;

a back support layer with an inner surface and an outer surface, where at least a portion of the inner surface includes an adhesive layer; and a separation layer affixed over at least a portion of the adhesive layer, where the separation layer is removable from the adhesive layer.

The method also includes applying a target coating composition over the first surface of the clearcoat layer to form a wet coating layer thereon. The wet coating layer is at least partially cured or dried to form the target coating layer, and characteristics of the target coating layer are measured from the second surface of the clearcoat layer.

BRIEF DESCRIPTION OF DRAWING

The present invention will hereinafter be described in conjunction with the following drawing figures, wherein like numerals denote like elements, and:

FIG. 1 shows examples of the system.

FIG. 2 shows further examples of the system.

FIG. 3 shows examples of the method and the system.

FIG. 4 show further examples of the system.

DETAILED DESCRIPTION

Figure 1A:
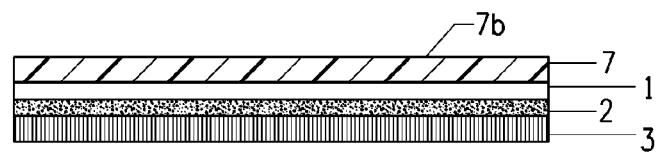
FIG. 1A is a side cross-sectional view of the system comprising a clearcoat layer (1), a removable front support layer (7), a target coating layer (2) and a back support layer (3).
Figure 1B:
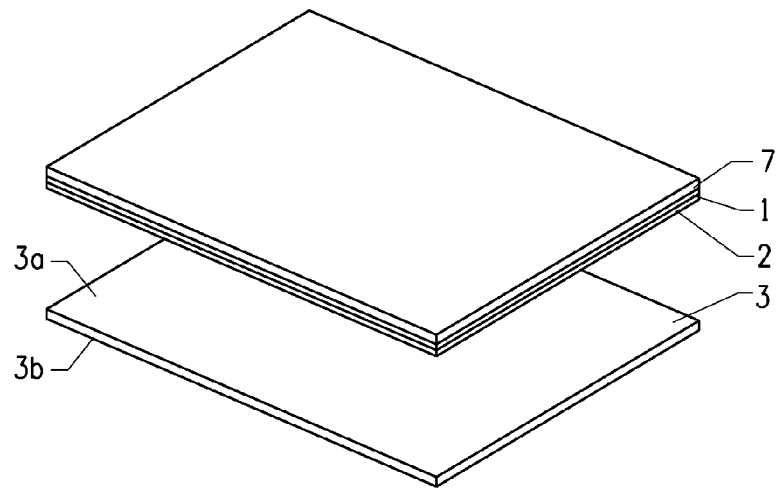
FIG. 1B is a schematic view of an example of the back support layer (3) prior to being assembled.
Figure 1C:
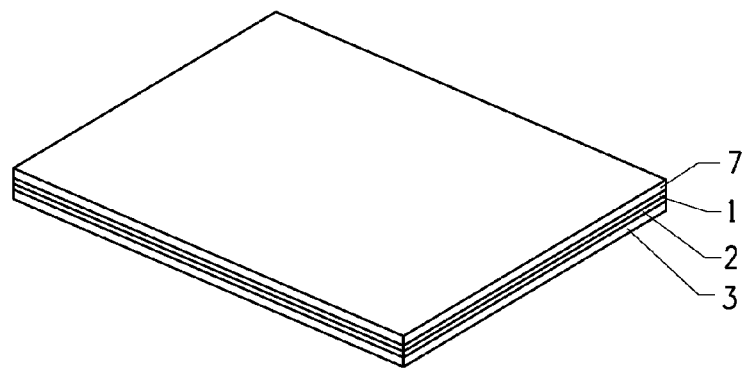
FIG. 1C is an example of an assembled system having the indicated layers.

The following detailed description is merely exemplary in nature and is not intended to limit the invention or the application and uses of the invention. Furthermore, there is no intention to be bound by any theory presented in the preceding background of the invention or the following detailed description.

The features and advantages of the present invention will be more readily understood, by those of ordinary skill in the art, from reading the following detailed description. It is to be appreciated that certain features of the invention, which are, for clarity, described above and below in the context of separate embodiments, may also be provided in combination in a single embodiment. Conversely, various features of the invention that are, for brevity, described in the context of a single embodiment, may also be provided separately or in any sub-combination. In addition, references in the singular may also include the plural (for example, "a" and "an" may refer to one, or one or more) unless the context specifically states otherwise.

The use of numerical values in the various ranges specified in this application, unless expressly indicated otherwise, are stated as approximations as though the minimum and maximum values within the stated ranges were both proceeded by the word "about." In this manner, slight variations above and below the stated ranges can be used to achieve substantially the same results as values within the ranges. Also, the disclosure of these ranges is intended as a continuous range including every value between the minimum and maximum values.

As used herein:

"Gloss" means surface gloss of a coating surface and is related to the amount of incident light that is reflected at the specular reflectance angle of the mean of that surface. Gloss can be measured with a specular glossmeter, such as those available from Byk-Gardener, Geretsried, Germany or other locations.

"DOI" (Distinctness of Image) is a quantitative measure of coating appearance that measures the light reflected at and around the specular reflectance angle. It can be determined according to the method described in ASTM D 5767. DOI can be measured with wave scan instruments, such as those available from Byk-Gardener, Geretsried, Germany or other locations. DOI measures not only the amount of incident light that is reflected at the specular reflectance angle, but also the distribution of the reflected light around the reflectance specular angle, typically +/−0.3° from the specular angle. A coating surface that gives fuzzy or distorted image generally produces a low DOI reading. A coating reflecting 100% of lights at the specular angle gives a DOI reading of 100.

The term "hiding" or "hiding power" refers to a coating composition's ability to cover a surface opaquely so that an underlying coating or substrate cannot be seen in visible light. For a pigmented coating composition, hiding typically increases with increasing thickness of the coating layer formed by the coating composition. Hiding can be determined with several known methods such as the method ASTM D 6762-02a. The minimum thickness of a coating layer for a complete hiding is referred to as a "hiding thickness". A hiding device can have different contrast patterns including high contrast patterns, such as black-and-white patterns.

The term "pigment" or "pigments" used herein refers to a colorant or colorants that produce color or colors. A pigment can be from natural and synthetic sources and can be made of organic or inorganic constituents. A pigment can also include metallic particles or flakes with specific or mixed shapes and dimensions. A pigment is usually not soluble in a coating composition.

The term "effect pigment" or "effect pigments" refers to pigments that produce special effects in a coating. Examples of effect pigments can include, but not limited to, light scattering pigments, light interference pigments, and light reflecting pigments. Flakes, such as metallic flakes, for example aluminum flakes, are examples of such effect pigments. Effect pigments can also include pearlescent pigments.

Gonioapparent flakes refer to flakes which change color or appearance, or a combination thereof, with changing in illumination angle or viewing angle. Metallic flakes, such as aluminum flakes are examples of gonioapparent flakes.

The term "dye" means a colorant or colorants that produce color or colors. Dye is usually soluble in a coating composition.

"Characteristics" of a coating used herein can include color characteristics and appearance characteristics.

The term "appearance" or "appearance characteristics" used herein can include: (1) the aspect of visual experience by which a coating is viewed or recognized; and (2) perception in which the spectral and geometric aspects of a coating is integrated with its illuminating and viewing environment. In general, appearance can include texture, sparkle, or other visual effects of a coating, especially when viewed from varying viewing angles and/or with varying illumination angles. Examples of appearance characteristics can also include, metallic effect, pearlescent effect, gloss, distinctness of image, coarseness, glint and glitter as well as the enhancement of depth or color perception in the coatings imparted by the effect pigments, especially produced by metallic flakes, such as aluminum flakes. Appearance characteristics can be obtained by visual inspection or by using an appearance measurement device.

The term "layer" or "layers" used herein refers to a sheet or a film, in which dimensions of width and length are greater than the dimension of its thickness, sometimes a few orders of magnitude greater. A layer can have two surfaces opposite to each other. A layer can be stand alone or affixed to a substrate or other materials. Examples of layers can include a coating layer, an aluminum foil, a plastic film, a foil formed from polymeric materials, a sheet of paper, or a sheet of glass.

Color characteristics of a coating can include visual aspects of color of the coating, chroma, hue, lightness, darkness, spectral reflectance, L, a, b, L*, a*, b*, X, Y, Z values, L, C, h values, and a combination thereof. The color characteristics can be obtained by visual inspection, or by using a color measurement device such as a colorimeter, a spectrophotometer, or a goniospectrophotometer.

The term "coating" or "coating composition" can include any coating compositions known to those skilled in the art and can include a two-pack coating composition, also known as "2K coating composition"; a one-pack or 1K coating composition; a coating composition having a crosslinkable component and a crosslinking component; a radiation curable coating composition, such as a UV curable coating composition or an E-beam curable coating composition; a mono-cure coating composition; a dual-cure coating composition; a lacquer coating composition; a waterborne coating composition or aqueous coating composition; a solvent borne coating composition; or any other coating compositions known to or developed by those skilled in the art. The coating composition can be formulated as a primer, a basecoat, or a color coat composition and can comprise dyes, pigments or effect pigments. The coating composition can also be formulated as a clearcoat composition. Clearcoat composition can further comprise certain pigments having same or similar optical properties, such as same or similar refractive index as the cured clearcoat. One of such pigments can be transparent silica.

The term "vehicle", "automotive", "automobile" or "automotive vehicle" can include an automobile, such as car, bus, truck, semi truck, pickup truck, SUV (Sports Utility Vehicle); tractor; motorcycle; trailer; ATV (all terrain vehicle); heavy duty mover, such as, bulldozer, mobile crane and earth mover; airplanes; boats; ships; and other modes of transport.

An imaging device refers to a device that can capture images under a wide range of electromagnetic wavelengths including visible or invisible wavelengths. Examples of the imaging device can include, but not limited to, a still film optical camera, a digital camera, an X-Ray camera, an infrared camera, an analog video camera, and a digital video camera. A digital imager or digital imaging device refers to an imaging device captures images in digital signals. Examples of the digital imager can include, but not limited to, a digital still camera, a digital video camera, a digital scanner, and a charge coupled device (CCD) camera. An imaging device can capture images in black and white, gray scale, or various color levels.

This invention is directed to a method for obtaining characteristics of a target coating layer. The method can comprise the steps of:
 a) providing a removable front support layer having a lower surface and an upper surface;
 b) providing a clearcoat layer having a first surface and a second surface, wherein at least a portion of said lower surface of the front support layer is affixed to said second surface of the clearcoat layer and removable from said clearcoat layer;
 c) applying a target coating composition over at least a portion of said first surface of the clearcoat layer to form a wet coating layer thereon;
 d) at least partially curing or drying said wet coating layer to form said target coating layer; and
 e) obtaining said characteristics of said target coating layer by measuring from the second surface of the clearcoat layer.

The removable front support layer can be produced from plastic, such as thermoplastic polymer or thermoset polymer. The removable front support layer can be a polyester (PE) film, a polyethylene terephthalate polyester (PET) film, a polyvinyl chloride (PVC) film, a polypropene (PP) film, a polystyrene (PS) film, a thermoplastic polyurethanes (TPU) film, or a combination thereof. The removable front support layer can also be produced from paper, other plastic or polymeric materials, metal, glass or any other suitable materials, or a combination thereof. A sheet of paper, a plastic film, a metal film such as an aluminum film or foil, or a combination thereof can be suitable. The removable front support layer can be flexible or non-flexible.

The removable front support layer (7) can have a lower surface (7a) and an upper surface (7b). The lower surface (7a) can be affixed over at least a portion of the second surface (1b) of the clearcoat layer (1). The removable front support layer (7) can be removed from the clearcoat layer and can comprise a release layer over the lower surface (7a) for easy removal of the front support layer from the clearcoat layer. In one example, the removable front support layer can be removed after the clearcoat layer is formed from the clearcoat composition. In another example, the removable front support layer can be removed after at least partially curing or drying the target coating layer. The release layer can comprise one or more fluoropolymers. Examples of the fluoropolymers can include polytetrafluoroethylene or derivatives therefrom. Examples of commercially available fluoropolymers can include Teflon® available from DuPont, Wilmington, USA, under registered trademark.

The front support layer can be colorless or colored. The front support layer can be transparent or non-transparent. The front support layer can also have patterns or patches of patterns.

The removable front support layer can have a thickness in a range of from 1 mil to 40 mils (about 25 µm to 1016 µm) in one example, from 5 mil to 30 mils (about 125 µm to 760 µm) in another example, and from 5 mil to 20 mils (about 125 µm to 508 µm) in yet another example.

Figure 2A:
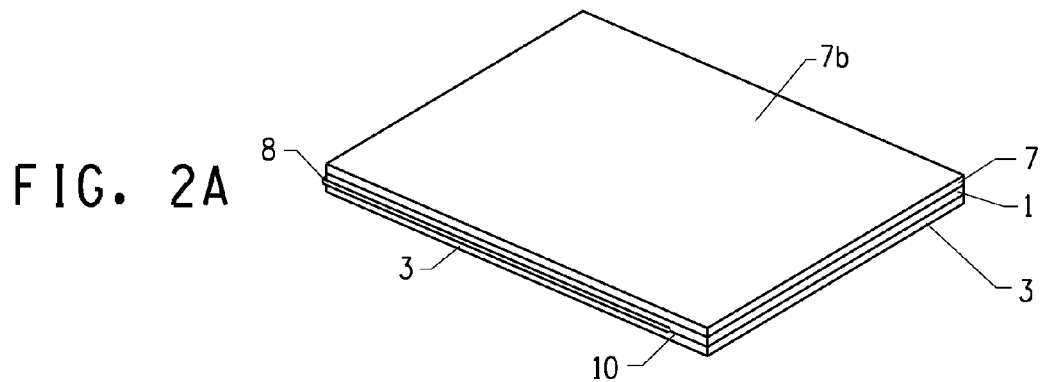
FIG. 2A is example of the system having a separation layer (8), a clearcoat layer (1), a removable front support layer (7) and a back support layer (3) assembled.
Figure 2B:
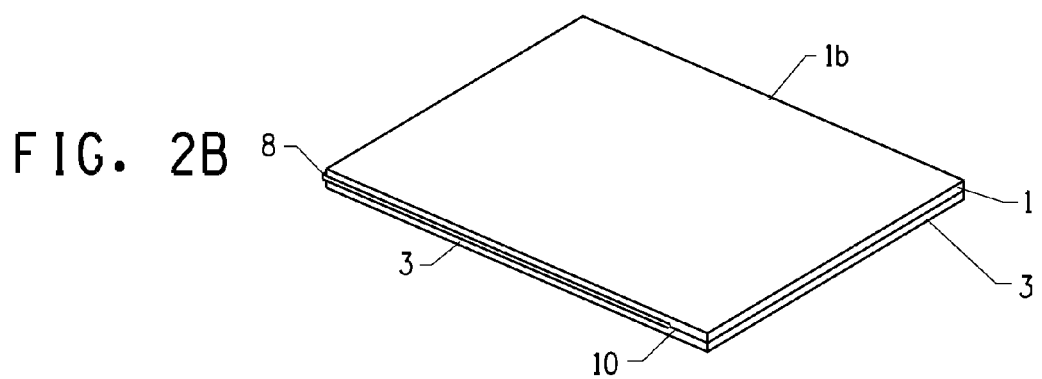
FIG. 2B is an example of the system without the removable front support layer (7).
Figure 2C:
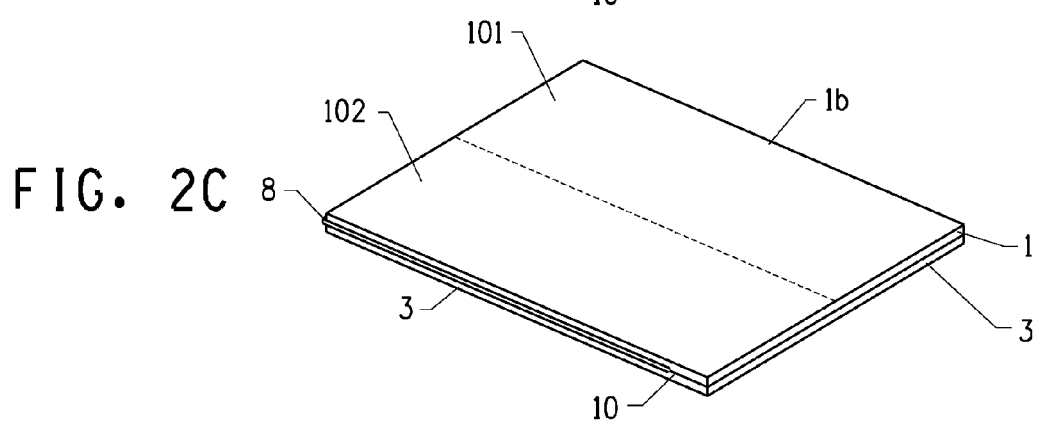
FIG. 2C and FIG. 2D are examples of the clearcoat layer having multiple portions.
Figure 2D:
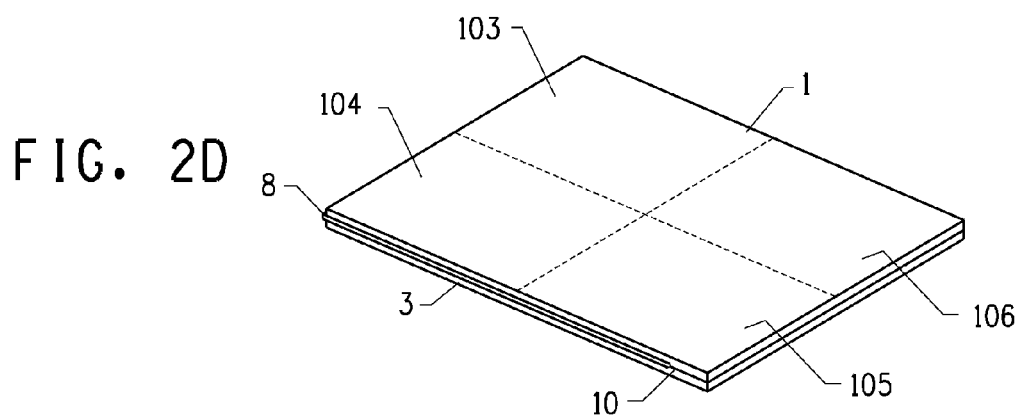
Figure 3A:
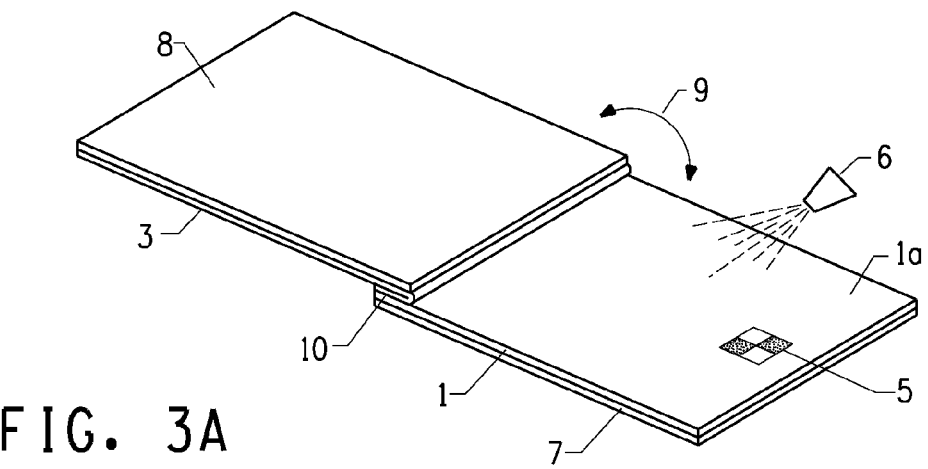
FIG. 3A is an example of the system in an open format with the target coating being applied.
Figure 3B:
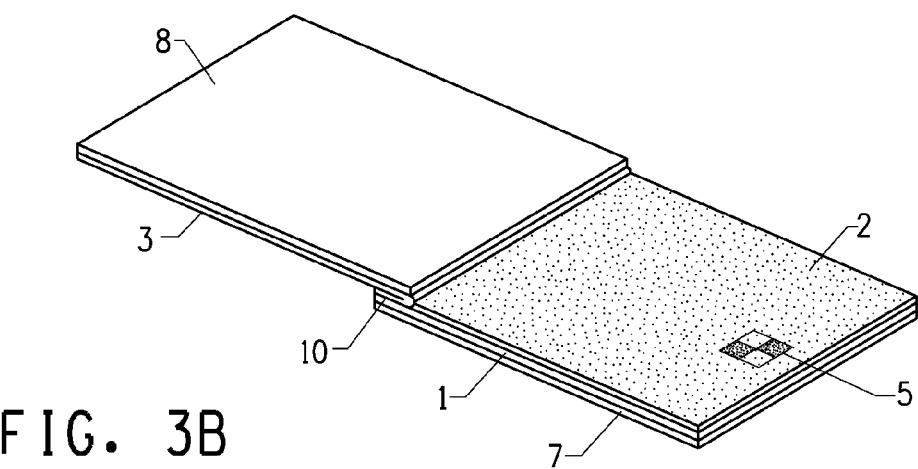
FIG. 3B is an example of the system with a target coating applied to a partial hiding.
Figure 3C:
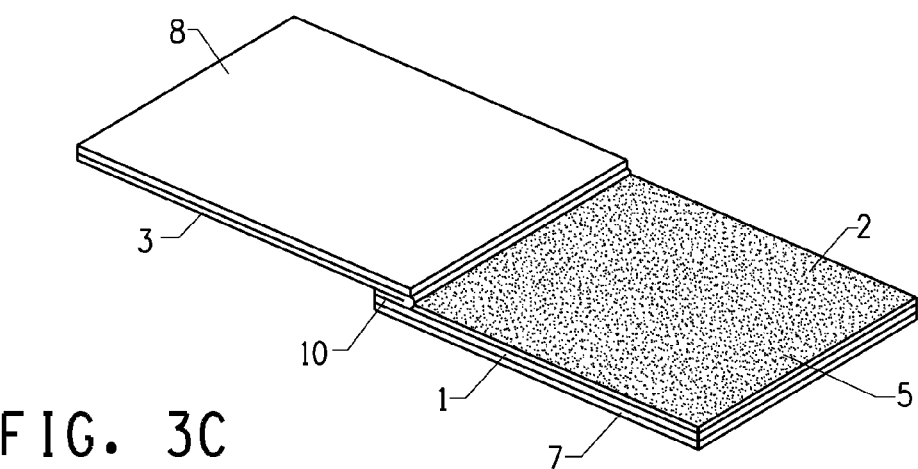
FIG. 3C is an example of the system with a target coating applied to a complete hiding.
Figure 3D:
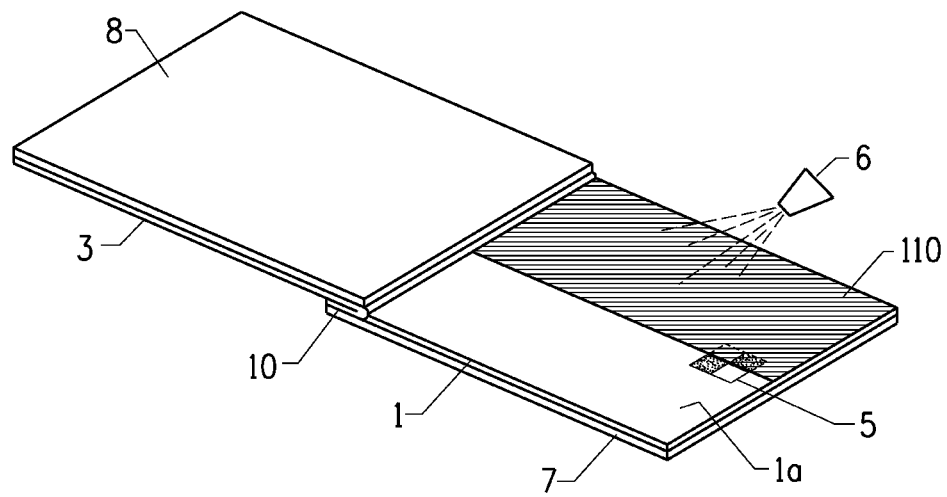
FIG. 3D and FIG. 3E are examples of the system having one or more target coatings applied.
Figure 3E:
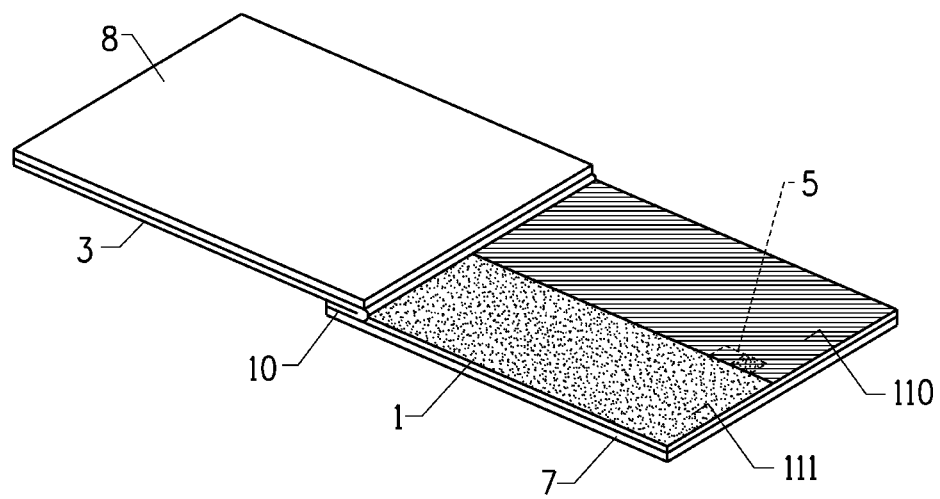

The clearcoat layer can have a range of gloss levels. The clearcoat layer can have a constant gloss level or a plurality of different gloss levels, or have patterns or strips of different gloss levels across the clearcoat layer. In one example, the clearcoat layer can have two portions (101) and (102) (FIG. 2C) each differing in gloss levels, thickness or a combination thereof. In another example, the clearcoat layer can have multiple portions (103-106) (FIG. 2D) having different gloss levels, different thicknesses, or a combination thereof. The clearcoat layer can also be colorless, tinted or colored.

The clearcoat layer can be produced by a process comprising the steps of:
 applying at least one clearcoat composition over at least a portion of said lower surface of said removable front support layer to form a wet clearcoat layer thereon; and
 curing said wet clearcoat layer to form said clearcoat layer.

The clearcoat layer can also be produced by a process comprising the step of:
 applying two or more clearcoat compositions over one or more portions of said lower surface of said removable front support layer to form said clearcoat layer.

The clearcoat layer can have different properties at different portions such as different colors, gloss levels, or combination thereof. The clearcoat layer can have a constant thickness or a plurality of different thicknesses. In one example, the clearcoat layer can have a constant thickness. In another example, the clearcoat layer can have a wedged variable thickness. In yet another example, the clearcoat layer can have one thickness at one portion and a different thickness at another portion of the clearcoat layer.

The clearcoat layer can comprise one or more clearcoat sub-layers formed from a single or a plurality of clearcoat compositions. In one example, the clearcoat layer can be formed from a single clearcoat composition with one or more sub-layers. In another example, the clearcoat layer can comprise one or more sub-layers formed from one or more different clearcoat compositions. In yet another example, the clearcoat layer can be formed from a single clearcoat composition with different thicknesses at different portions. In yet another example, the clearcoat layer can have one portion formed from one clearcoat composition and a subsequent portion formed from a different clearcoat composition. In yet another example, the clearcoat layer can be formed from two or more clearcoat compositions applied over one or more portions of the lower surface of the removable front support layer.

Any clearcoat compositions known to or developed by those skilled in the art can be suitable for forming the clearcoat layer. Examples of the clearcoat compositions can include two-pack coating composition, one-pack coating composition, coating composition having a crosslinkable component and a crosslinking component, radiation curable coating, mono-cure coating, dual-cure coating, lacquer coating, waterborne coating, or solvent borne coating. Suitable clearcoat compositions can further comprise suitable pigments or other components, such as silica or other transparent pigments. The clearcoat composition can have one or more additives to produce the clearcoat layer having different properties, such as scratch resistance, different levels of gloss, ultraviolet (UV) resistance, or a combination thereof. One example of the additives can include silica or silica derivatives. Further examples of additives can include ultraviolet (UV) light stabilizers, ultraviolet light absorbers, screeners, quenchers, antioxidant, wetting agents, leveling and flow control agents, rheological control agents, flatteners, thickeners, or catalysts. The additives can be used in conventional amounts familiar to those skilled in the art.

The clearcoat composition can also be tinted or colored. In one example, the clearcoat composition can be tinted with one or more tints or other pigments. In another example, the clearcoat composition can be colored with one or more pigments, tints, dyes, or a combination thereof. The clearcoat composition can also have one or more components same or different from the target coating composition mentioned herein. In one example, the clearcoat composition and the target coating composition can have one or more same or different binder components. In another example, the clearcoat composition and the target coating composition can have one or more same or different flatteners.

The clearcoat composition can comprise a polytrimethylene ether diol having a Mn (number average molecular weight) in a range of from 500 to 10,000. Suitable polytrimethylene ether diol can be prepared by an acid-catalyzed polycondensation of 1,3-propanediol, such as described in U.S. Pat. Nos. 6,977,291 and 6,720,459. A bio-route via fermentation of a renewable resource can be used to obtain the 1,3-propanediol. One example of renewable resources is corn since it is readily available and has a high rate of conversion to 1,3-propanediol and can be genetically modified to improve yields to the 1,3-propanediol. Examples of typical bio-route can include those described in U.S. Pat. No. 5,686,276, U.S. Pat. No. 5,633,362 and U.S. Pat. No. 5,821,092. Addition of the polytrimethylene ether diol can enhance flexibility of the clearcoat layer, therefore preventing cracking, chipping or other damage to the clearcoat layer during operation.

Curing of the clearcoat layer can be done at a temperature, time and other conditions suitable for the chosen clearcoat composition. In one example, the clearcoat can be cured at a temperature in a range of from 15° C. to 60° C. For a radiation curable coating, the clearcoat can be exposed to an appropriate radiation source, such as a UV light or e-beam, for a certain period of time suitable for the chosen clearcoat composition.

The clearcoat composition can be applied using any of the coating application techniques known to or developed by those skilled in the art.

The clearcoat layer is transparent and can be colorless, colored or tinted. The clearcoat layer can have a thickness in a range of from 0.1 mil to 40 mils (about 2.5 µm to 1016 µm) in one example, from 0.5 mil to 30 mils (about 12.5 µm to 760 µm) in another example, from 0.5 mil to 20 mils (about 12.5 µm to 508 µm) in yet another example, from 0.5 mil to 10 mils (about 12.5 µm to 254 µm) in yet another example, and from 0.5 mil to 5 mils (about 12.5 µm to 127 µm) in yet another example.

The target coating composition can be any one of the aforementioned coating compositions, such as a two-pack coating composition, a one-pack coating composition, a coating composition having a crosslinkable component and a crosslinking component, a radiation curable coating, a mono-cure coating, a dual-cure coating, a lacquer coating, a water-borne coating, or a solvent borne coating. For a two-pack coating composition, two packages of the coating composition can be mixed immediately prior to applying the coating.

The target coating composition can comprise one or more pigments, one or more effect pigments, or a combination thereof. The effect pigments can comprise one or more metallic pigments, one or more pearlescent pigments, or a combination thereof. Examples of the effect pigment can include aluminum flakes or pearlescent pigments.

The target coating composition can be applied using spraying, brushing, rolling, draw down, or any other conventional coating application techniques known to those skilled in the art. A hiding mark (5), such as the ones available from THE LENETA COMPANY, INC., Mahwah, N.J., USA, can be used to monitor spraying thickness of the target coating layer. The hiding mark can be affixed to the clearcoat layer before applying the target coating layer. The hiding mark can also be placed between the clearcoat layer and the removable front support layer and visible through the clearcoat layer.

The target coating layer can be at least partially cured or partially dried. The target coating layer can also be completely cured or dried. The term "partially curing" or "partially drying" means curing or drying the wet coating layer for a time period that is shorter than the time period required for complete curing or drying of the coating layer. Typically, a short period of time such as in a range of from a few seconds to a few hours can be suitable for at least partially curing or drying a wet coating layer. The target coating layer can be at least partially cured or partially dried at a temperature in a range of from 15° C. to 60° C.

Time or temperature that is required for complete curing or drying the target coating layer can be dependent upon the target coating composition being used. In one example, a few minutes can be suitable for curing or drying one target coating layer. In another example, 10 to 60 minutes can be suitable for curing or drying another target coating layer. In yet another example, a few hours, such as 1 to 20 hours can be suitable for curing or drying yet another target coating layer. In further example, a few days, such as 1 to 7 days can be suitable for curing or drying further another coating layer. For a radiation curable coating, the wet coating layer can be exposed to an appropriate radiation source, such as a UV light or e-beam, for a certain period of time.

The target coating layer can be formed from one or more same or different target coating compositions and can be covering the same or different portions of the clearcoat layer (110-111) (FIG. 3 D-E). The target coating layer can be applied in uniform or different thicknesses. The target coating layer can also comprise one or more coating layers formed from the same or different coating compositions.

The method of this invention can further comprise the step of applying a back support layer (3) having an inner surface (3*a*) and an outer surface (3*b*) over the target coating layer with the inner surface (3*a*) close to the target coating layer. The target coating layer can be positioned between the clearcoat layer and the back support layer.

The back support layer can be made from paper, plastic, polymeric materials, metal, glass or any other suitable materials. The back support layer can be flexible or non-flexible.

The back support layer can comprise a primer layer. Any coating composition suitable for use as a primer can be suitable for forming this primer layer. The primer layer can have one or more layers formed from the same or different coating compositions suitable for use as primers. A primer layer with good hiding property is preferred. In one example, the primer layer can be a grey primer layer. If the back support layer is transparent or semi-transparent, the primer layer can be at either of the two surfaces of the back support layer. If the back support layer is non-transparent, the primer layer can be preferably positioned on the surface of the back support layer facing toward the target coating layer. It can be preferred that the back support layer is non-transparent if the back support layer does not comprise the primer layer or the primer layer has incomplete hiding.

The back support layer can comprise an adhesive layer. Any adhesives or pressure-sensitive adhesives can be suitable. The adhesive layer can be optional. When present, the adhesive layer can be positioned over the inner surface (3a) of the back support layer so that the back support layer can be bound to the target coating layer via said adhesive layer. In the absence of the adhesive layer, the back support layer can be stacked together with the clearcoat layer so that the target coating layer can be positioned in between. When the adhesive layer is present, the back support layer can further comprise a separation layer (8) to protect the adhesive layer prior to binding of the back support layer and the target coating layer.

The back support layer can comprise a magnetic layer. Any magnetic materials that can form a magnetic layer can be suitable. It is preferred that the magnetic layer is flexible. The commercial available magnetic labels comprising magnets or magnetic polymers can be suitable. In one example, the magnetic layer can form the base of the back support layer wherein the primer layer or the adhesive layer can be applied thereon. In another example, the back support layer can comprise a primer layer, an adhesive layer, a magnetic layer, or a combination thereof.

Figure 4A:
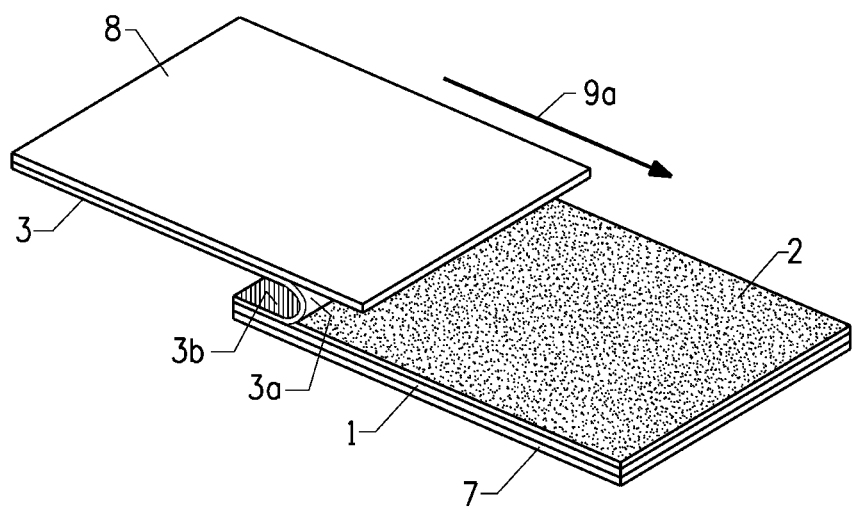
FIG. 4A is a schematic view of the system with the separation layer (8) being removed and the back support layer (3) being applied to the target coating layer (2).

The back support layer can be applied to the target coating layer by removing the separation layer (8) therefore exposing the adhesive layer and subsequent binding of the back support layer and the target coating layer. In one example, the back support layer having an adhesive layer can be applied by peeling off the separation layer (8) in the direction (9a) (FIG. 4A) and applying pressure from the outer surface (3b) towards the target coating layer (2).

Figure 1D:
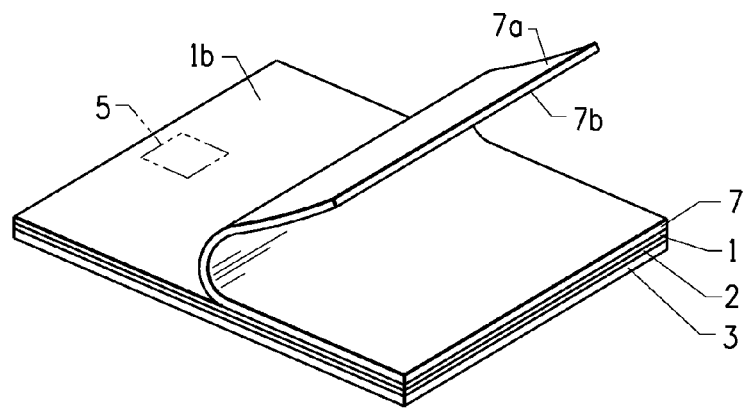
FIG. 1D is a schematic view of the removal of the removable front support layer (7).
Figure 4B:
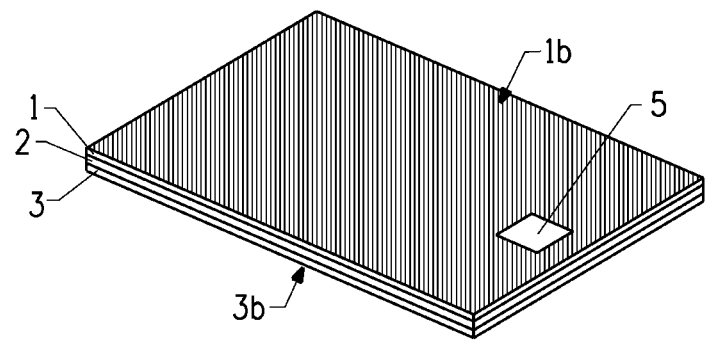
FIG. 4B is a schematic view of the system with target coating layer (2) applied, the removable front support layer (7) removed and the clearcoat layer facing up.

The removable front support layer (7) can be removed after the back support layer (3) is applied (FIG. 1D and FIG. 4B).

The characteristics of the target coating layer (2) can be measured from the second surface (1b) and can be color characteristics, appearance characteristics, or a combination thereof. The characteristics can be obtained by using a color measuring device, an appearance measuring device, or a color-appearance dual measuring device. The color measuring device, the appearance measuring device, or the color-appearance dual measuring device can comprise an imaging device. Examples of the color measurement device can include, such as a colorimeter, a spectrophotometer, or a goniospectrophotometer. The characteristics can also be obtained by visual inspection or observation. The characteristics can be obtained under one or more illumination conditions, including, nut not limited to, illumination light intensities, illumination spectral power distributions, illumination light angles, and a combination thereof. One or more viewing/measurement angles, such as 15°/25°/45°/75°/110° and optionally −15°, can be suitable.

The color characteristics can comprise visual aspects of color of the coating, chroma, hue, lightness, darkness, spectral reflectance, L, a, b, L*, a*, b*, X, Y, Z values, or L, C, h values, or a combination thereof. Spectral reflectance, L, a, b, L*, a*, b*, X, Y, Z values, or L, C, h values, or a combination thereof can be preferred. The appearance characteristics can include, but not limited to, gloss, distinctness of image, coarseness, flake appearances such as texture, sparkle, glint and glitter as well as the enhancement of depth perception in the coatings imparted by the flakes, especially produced by metallic flakes, such as aluminum flakes.

The appearance characteristics can include texture, sparkle, metallic effect, pearlescent effect, gloss, distinctness of image, coarseness, glint and glitter, the enhancement of depth or color perception in the coatings imparted by the effect pigments, or a combination thereof. The appearance characteristics can further include other visual effects of a coating. The appearance characteristics can be obtained by visual inspection or by using an appearance measurement device.

Figure 5:
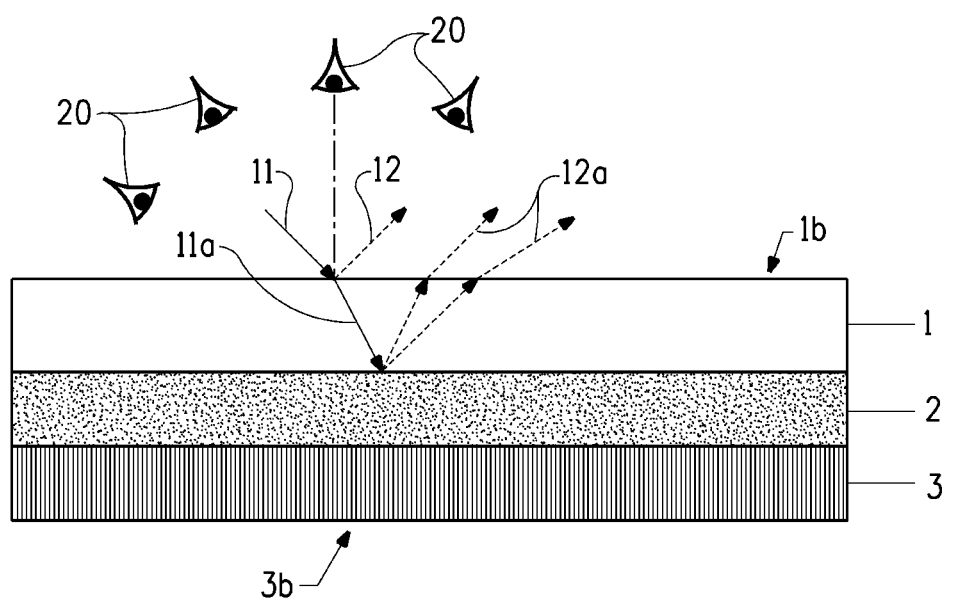
FIG. 5 shows a schematic presentation of one example of illumination and measurement of the target coating layer.

The characteristics of the target coating layer can be obtained by measuring from the second surface of the clearcoat layer and through the clearcoat layer. When the removable front support layer is transparent, the characteristics can be obtained with or without the removable front support layer. It is preferred to remove the removable front support layer prior to obtaining the characteristics of the target coating. One example is shown in FIG. 5. Illumination light (11) can be provided as defused light or at an illumination angle appropriate for the measurement, such as 45°, and can produce reflections from the clearcoat layer's surface (12). Part of the illumination light (11) can travel through the clearcoat layer (1) becoming a refracted light (11a) and can produce reflections from the target coating layer surface (12a). Characteristics of the target coating layer (2) can be obtained by measuring from the second surface (1b) of the clearcoat layer (1) at one or more viewing or measurement points (20). Depending on the surfaces, reflections can be unidirectional or multidirectional. For a high gloss clearcoat, reflections can be unidirectional or very close to unidirectional. For a low gloss or matt coating surface, reflections can be multidirectional. Multi-angle measurement devices that are commercially available can be used to measure the characteristics of the target coating.

In traditional method, in order to measure characteristics of a target coating layer that is protected with a clearcoat, the target coating layer needs to be applied first. Then a clearcoat is applied over the target coating layer. The target coating layer and the clearcoat layer can be cure sequentially or simultaneously. Traditional method requires extra time and effort for applying and curing the clearcoat layer.

The method of this disclosure provides an advantage of fast and accurate measurement of the characteristics of the target coating layer. The clearcoat layer can be premade. Only the formation of the target coating layer is needed, therefore reducing the measurement time and effort. In addition, since the clearcoat layer is formed from a clearcoat composition, the measurement can be more accurate than earlier attempts that use plastic films such as Mylar polyester film. One of such earlier attempts can include the one described in U.S. Pat. No. 5,371,599.

This invention is also directed to a system for obtaining characteristics of a target coating layer. The system can comprise:

i) a clearcoat layer (1) having a first surface (1a) and a second surface (1b);

ii) a removable front support layer (7) having a lower surface (7a) and an upper surface (7b), said a lower surface (7a) of the removable front support layer (7) is affixed over at least a portion of said second surface of the clearcoat layer;

iii) a back support layer (3) having an inner surface (3a) and an outer surface (3b), at least a portion of said inner surface comprises an adhesive layer thereon; and iv) a separation layer (8) affixed over at least a portion of said adhesive layer, said separation layer is removable from said adhesive layer.

The removable front support layer and said back support layer can be assembled at a joint edge (10) with said lower surface (7a) facing said inner surface (3a), said clearcoat layer and said separation layer can be positioned between said removable front support layer and said back support layer, and wherein said removable front layer and said back support layer can be pivotable around said joint edge to expose said first surface (1a) of the clearcoat layer.

Aforementioned clearcoat layer, removable front support layer, back support layer, and separation layer can be suitable.

The system can comprise a color measurement device, an appearance measurement device, a color-appearance dual measuring device, or a combination thereof. The system can further comprise an aforementioned hiding mark.

This disclosure is further directed to a method for obtaining characteristics of a target coating layer using the system disclosed herein. The method can comprise the steps of:

A) providing a measurement system comprising;
  i) a clearcoat layer (1) having a first surface (1a) and a second surface (1b);
  ii) a removable front support layer (7) having a lower surface (7a) and an upper surface (7b), said a lower surface (7a) of the removable front support layer (7) is affixed over at least a portion of said second surface of the clearcoat layer;
  iii) a back support layer (3) having an inner surface (3a) and an outer surface (3b), at least a portion of said inner surface comprises an adhesive layer thereon; and
  iv) a separation layer (8) affixed over at least a portion of said adhesive layer, said separation layer is removable from said adhesive layer;
B) applying a target coating composition over said first surface of the clearcoat layer to form a wet coating layer thereon;
C) at least partially curing or drying said wet coating layer to form said target coating layer; and
D) obtaining said characteristics of said target coating layer by measuring from the second surface of the clearcoat layer.

The method can further comprise the step of removing said removable front support layer prior to obtaining the characteristics of said target coating layer.

The target coating composition comprises one or more pigments, one or more effect pigments, or a combination thereof. The effect pigments can comprise one or more metallic pigments, one or more pearlescent pigments, or a combination thereof.

The wet coating layer can be cured at a temperature in a range of from 15° C. to 60° C. The characteristics can be color characteristics, appearance characteristics, or a combination thereof. The characteristics can be obtained by using a color measuring device, an appearance measuring device, a color-appearance dual measuring device, or a combination thereof.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. A system comprising:
  i) a clearcoat layer (1) having a first surface (1a) and a second surface (1b);
  ii) a removable front support layer (7) having a lower surface (7a) and an upper surface (7b), said lower surface (7a) of the removable front support layer (7) is affixed over at least a portion of said second surface of the clearcoat layer (1);
  iii) a back support layer (3) having an inner surface (3a) and an outer surface (3b), at least a portion of said inner surface comprises an adhesive layer thereon; and
  iv) a separation layer (8) affixed over at least a portion of said adhesive layer, said separation layer is removable from said adhesive layer.

2. The system of claim 1, wherein said removable front support layer and said back support layer are assembled at a joint edge (10) with said lower surface (7a) facing said inner surface (3a), said clearcoat layer and said separation layer are positioned between said removable front support layer and said back support layer, and wherein said removable front layer and said back support layer are pivotable around said joint edge to expose said first surface (1a) of the clearcoat layer.

3. The system of claim 1, wherein said removable front support layer is produced from thermoplastic polymer, thermoset polymer, paper, metal, glass, or a combination thereof.

4. The system of claim 1, wherein said removable front support layer is a polyester (PE) film, a polyethylene terephthalate polyester (PET) film, a polyvinyl chloride (PVC) film, a polypropene (PP) film, a polystyrene (PS) film, or a thermoplastic polyurethanes (TPU) film, a metal film, or a combination thereof.

5. The system of claim 1, wherein said clearcoat layer is produced by a process comprising the steps of:
  applying a clearcoat composition over said lower surface (7a) of the front support layer to form a wet clearcoat layer; and
  curing said wet clearcoat layer to form said clearcoat layer.

6. The system of claim 1, wherein said clearcoat layer is produced by a process comprising the step of:
  applying two or more clearcoat compositions over one or more portions of said lower surface of said removable front support layer to form said clearcoat layer.

7. The system of claim 1, wherein said back support layer comprises a primer layer.

8. The system of claim 1, wherein said back support layer comprises a magnetic layer.

9. The system of claim 1 further comprising a color measurement device, an appearance measurement device, a color-appearance dual measuring device, or a combination thereof, wherein said color measurement device, said appearance measurement device, said color-appearance dual measuring device, or said combination thereof are configured to obtain a color characteristic or an appearance characteristic of said second surface.

10. The system of claim 1 further comprising a hiding mark.

11. The system of claim 1, wherein said clearcoat layer has a constant thickness, a plurality of different thicknesses, a constant gloss level, a plurality of different gloss levels, or a combination thereof.

12. The system of claim 1, wherein said clearcoat layer is colorless, colored, or tinted.

13. The system of claim 1, wherein said clearcoat layer is formed from a clearcoat composition comprising a polytrimethylene ether diol polymerized from bio-derived 1,3-propanediol.

14. A method for obtaining characteristics of a target coating layer, said method comprising the steps of:
- A) providing a measurement system comprising;
  - i) a clearcoat layer (1) having a first surface (1a) and a second surface (1b);
  - ii) a removable front support layer (7) having a lower surface (7a) and an upper surface (7b), said lower surface (7a) of the removable front support layer (7) is affixed over at least a portion of said second surface of the clearcoat layer;
  - iii) a back support layer (3) having an inner surface (3a) and an outer surface (3b), at least a portion of said inner surface comprises an adhesive layer thereon; and
  - iv) a separation layer (8) affixed over at least a portion of said adhesive layer, said separation layer is removable from said adhesive layer;
- B) applying a target coating composition over said first surface of the clearcoat layer to form a wet coating layer thereon;
- C) at least partially curing or drying said wet coating layer to form said target coating layer; and
- D) obtaining said characteristics of said target coating layer by measuring from the second surface of the clearcoat layer.

15. The method of claim 14 further comprising the step of removing said removable front support layer prior to obtaining the characteristics of said target coating layer.

16. The method of claim 14, wherein said target coating composition comprises one or more pigments, one or more effect pigments, or a combination thereof.

17. The method of claim 16, wherein said effect pigments comprise one or more metallic pigments, one or more pearlescent pigments, or a combination thereof.

18. The method of claim 14, wherein said wet coating layer is cured at a temperature in a range of from 15° C. to 60° C.

19. The method of claim 14, wherein said characteristics are color characteristics, appearance characteristics, or a combination thereof.

20. The method of claim 14, wherein said characteristics are obtained by using a color measuring device, an appearance measuring device, a color-appearance dual measuring device, or a combination thereof.

* * * * *